United States Patent
Marks et al.

(10) Patent No.: US 9,403,737 B2
(45) Date of Patent: Aug. 2, 2016

(54) FORMING ETHYLENE

(75) Inventors: Tobin Marks, Evanston, IL (US); Qingjun Zhu, Evanston, IL (US); Staci Wegener, Evanston, IL (US)

(73) Assignee: Northwestern University, Evanston, IL (US)

( * ) Notice: Subject to any disclaimer, the term of this patent is extended or adjusted under 35 U.S.C. 154(b) by 198 days.

(21) Appl. No.: 14/233,211

(22) PCT Filed: Jul. 18, 2012

(86) PCT No.: PCT/US2012/047110
§ 371 (c)(1),
(2), (4) Date: Jan. 16, 2014

(87) PCT Pub. No.: WO2013/012883
PCT Pub. Date: Jan. 24, 2013

(65) Prior Publication Data
US 2014/0200383 A1    Jul. 17, 2014

Related U.S. Application Data

(60) Provisional application No. 61/508,712, filed on Jul. 18, 2011.

(51) Int. Cl.
C07C 2/84 (2006.01)
B01J 27/04 (2006.01)
B01J 27/045 (2006.01)
B01J 27/051 (2006.01)

(52) U.S. Cl.
CPC .. C07C 2/84 (2013.01); B01J 27/04 (2013.01); B01J 27/045 (2013.01); B01J 27/051 (2013.01); B01J 27/0515 (2013.01); C07C 2527/04 (2013.01); C07C 2527/045 (2013.01); C07C 2527/051 (2013.01); Y02P 20/52 (2015.11)

(58) Field of Classification Search
CPC .................................. C07C 1/20; C07C 1/00
See application file for complete search history.

(56) References Cited

U.S. PATENT DOCUMENTS

| | | | |
|---|---|---|---|
| 4,620,057 A | 10/1986 | Kimble et al. | |
| 4,864,073 A | 9/1989 | Han et al. | |
| 5,157,189 A * | 10/1992 | Karra | C01B 3/386 585/415 |
| 2010/0331595 A1 | 12/2010 | Chinta et al. | |

FOREIGN PATENT DOCUMENTS

| | | |
|---|---|---|
| CN | 1087291 | 6/1994 |
| EP | 0565101 | 10/1993 |
| WO | 9520556 | 8/1995 |

OTHER PUBLICATIONS

Anderson et al. "Reaction of methane and sulfur: oxidative coupling and carbon-disulfide formation." React. Kinet. Catal. Lett. 49, 261-269 (1993).*
Didenko et al. "Partial catalytic oxidation and condensation of methane by oxygen and sulfur" Catal. Today 42, 367-370 (1998).*
V.I. Savchenko, et al., "Interaction Between Methane and Sulfur with the Formation of Partial Oxidation and Oxidative Coupling Products" Institute of Chemical Physics in Chernogolovka, Russian Academy of Sciences, Dec. 29, 1994 (6 pgs).
International Search Report and Written Opinion from related PCT Application PCT/US2012/047110, filed Jul. 18, 2012, 9 pgs.

* cited by examiner

*Primary Examiner* — In Suk Bullock
*Assistant Examiner* — Sharon Pregler
(74) *Attorney, Agent, or Firm* — Brooks, Cameron & Huebsch, PLLC

(57) ABSTRACT

Form ethylene via a method that includes vaporizing elemental sulfur, providing a metal sulfide catalyst, and contacting the metal sulfide catalyst with a mixture of methane and the vaporized elemental sulfur to form ethylene. The mixture has a methane to sulfur molar ratio greater than 1.2:1.0.

6 Claims, No Drawings

FORMING ETHYLENE

This application is a National Stage Application under 35 U.S.C. §371 of International Application Number PCT/US2012/047110, filed Jul. 18, 2012 and published as WO 2013/012883 on Jan. 24, 2013, which claims the benefit of U.S. Provisional Application 61/508,712, filed Jul. 18, 2011, the entire contents of which are incorporated herein by reference in its entirety.

This disclosure relates to methods of forming ethylene, and in particular forming ethylene from methane.

Ethylene is a commodity chemical that is used as a building block for the chemical industry. Ethylene is used to manufacture products including, but not limited to, food packaging, eyeglasses, cars, medical devices, lubricants, engine coolants, and liquid crystal displays.

One current process of ethylene formation is oxidative methane coupling employing oxygen as an oxidant. In this oxidative methane coupling process, methane is activated heterogeneously on a catalyst surface and generally thought to form methyl free radicals, which then couple in the gas phase to form ethane. The ethane subsequently undergoes dehydrogenation to form ethylene. However, oxidative methane coupling employing oxygen as the oxidant has shown poor selectively to ethylene formation, as well as undesirable over-oxidation to carbon dioxide.

This disclosure provides a method of forming ethylene including vaporizing elemental sulfur, providing a metal sulfide catalyst, and contacting the metal sulfide catalyst with a mixture of methane and the vaporized elemental sulfur to form ethylene. The mixture has a methane to sulfur molar ratio greater than 1.2:1.0. The vaporized elemental sulfur is employed as an oxidant for oxidative methane coupling to ethylene. Advantageously, the method provides desirable ethylene selectivity and methane conversion.

"Elemental sulfur" refers to an allotropic form of sulfur. Elemental sulfur may consist predominantly of crown-shaped $S_8$ molecules. However, other forms and/or allotropes of sulfur are known and are considered elemental sulfur. For example, via processing, elemental sulfur containing $S_6$, $S_7$, $S_9$, $S_{10}$, $S_{11}$, $S_{12}$, or up to $S_{18}$ rings, linear, and/or branched configurations, can be formed. Elemental sulfur may be crystalline or amorphous.

The method includes vaporizing elemental sulfur. The method conditions include an elemental sulfur vaporization temperature that is equal to or greater than 200 degrees Celsius (° C.). For example, the elemental sulfur vaporization temperature may be within a range of from 200° C. to 1000° C. A preferred elemental sulfur vaporization temperature is within a range of from 200° C. to 650° C.

The method includes providing a metal sulfide catalyst. Examples of the metal sulfide catalyst include, but are not limited to, palladium sulfide, palladium subsulfides, molybdenum sulfide, titanium sulfide, ruthenium sulfide, tantalum sulfide, and combinations thereof "Sulfide" refers to compounds that include sulfur in its lowest oxidation state of −2. "Subsulfide" refers to compounds that include sulfur in an oxidation state other than −2. Examples of palladium subsulfides include, but are not limited to, $Pd_4S$, $Pd_3S$ and $Pd_{16}S_7$. These catalysts can be used in neat form or dispersed on supports such as alumina, silica, etc.

The method includes contacting the metal sulfide catalyst with a mixture of methane and the vaporized elemental sulfur to form ethylene. The mixture of methane and vaporized elemental sulfur can have a methane to sulfur molar ratio that is greater than 1.2:1.0. For example, the mixture of methane and vaporized elemental sulfur can have a methane to sulfur molar ratio that is in a range of from greater than 1.2:1.0 to 8.5:1.0. A preferred methane to sulfur molar ratio for the mixture is within a range of from greater than 1.2:1.0 to 5.8:1.0.

The method conditions include a reaction temperature, e.g., the temperature at which the mixture of methane and the vaporized elemental sulfur contact the metal sulfide catalyst. The reaction temperature may be within a range of from 200° C. to 2000° C. A preferred reaction temperature is within a range of from 825° C. to 1325° C.

The method may include supplying an inert gas to transport the mixture of methane and the vaporized elemental sulfur to the metal sulfide catalyst. Examples of the inert gas include, but are not limited to, argon, helium, nitrogen, and combinations thereof.

The method conditions include a weight hourly space velocity (WHSV), which is defined as a mass flow rate of feed per mass of catalyst. For example, the WHSV may be calculated as a mass of the methane in grams per hour divided by a mass of the metal sulfide catalyst in grams. The WHSV is within a range of from 6000 milliliters per inverse grams inverse hours ($mL \cdot g^{-1} \cdot h^{-1}$) to 30000 $mL \cdot g^{-1} \cdot h^{-1}$.

EXAMPLES

Materials include methane (Airgas, Inc.); argon (Airgas, Inc.); elemental sulfur (Sigma-Aldrich®); metal sulfide catalysts: molybdenum disulfide (Sigma-Aldrich®); titanium disulfide (Sigma-Aldrich®); ruthenium disulfide (Sigma-Aldrich®); tantalum disulfide (Sigma-Aldrich®); palladium sulphide (Alfa Aesar®). Equipment includes a heterogeneous catalytic reactor system (Altamira Instruments) having a vapor generator, a rector preheater, and a tubular reactor.

Example (Ex) 1

Load palladium sulfide catalyst (100 milligrams (mg)) into a tubular reactor (4 millimeter inner diameter) and elemental sulfur (50 grams (g)) into a vapor generator. Purge the reactor system with argon (25 milliliters per minute (mL/min)) for one hour. Maintain argon flow (25 mL/min) to the reactor system and heat reactor system components to desired temperatures at 10° C./minute: heat the vapor generator to 208° C. to vaporize the elemental sulfur; heat the reactor preheater to 650° C.; and heat the tubular reactor to 800° C. The vapor generator provides an argon and sulfur vapor mixture that is 0.85 mole percent sulfur. Combine a methane (25.0 mL/min) and argon mixture (10 mole percent methane) with the argon and sulfur vapor mixture and form a mixture of methane and the vaporized elemental sulfur and feed to the tubular reactor to contact the palladium sulfide catalyst and form ethylene. The mixture of methane and the vaporized elemental sulfur has a methane to sulfur molar ratio of 5.8:1.0. The WHSV is 30000 $mL \cdot g^{-1} \cdot h^{-1}$. Maintain conditions for three hours to ensure steady state. Pass reactor output through a sulfur condenser to remove sulfur and then separate and analyze products with an Agilent 7890 Gas Chromatography system including a flame ionization detector, a thermal conductivity detector, and a flame photometric detector. The analysis indicates that ethylene, carbon disulfide, and hydrogen sulfide were formed.

Exs 2-5

Repeat Ex 1, but with changes: heat the tubular reactor to 850° C.; 900° C.; 950° C.; and 1000° C., respectively.

Exs 6

Repeat Ex 1, but with changes: load molybdenum disulfide catalyst (100 mg) into tubular reactor rather than palladium sulfide catalyst.

Exs 7-10

Repeat Ex 6, but with changes: heat the tubular reactor to 850° C.; 900° C.; 950° C.; and 1000° C., respectively.

Exs 11

Repeat Ex 1, but with changes: load ruthenium disulfide catalyst (100 mg) into tubular reactor rather than palladium sulfide catalyst.

Exs 12-15

Repeat Ex 11, but with changes: heat the tubular reactor to 850° C.; 900° C.; 950° C.; and 1000° C., respectively.

Exs 16

Repeat Ex 1, but with changes: load titanium disulfide catalyst (100 mg) into tubular reactor rather than palladium sulfide catalyst.

Exs 17-20

Repeat Ex 16, but with changes: heat the tubular reactor to 850° C.; 900° C.; 950° C.; and 1000° C., respectively.

Exs 21

Repeat Ex 1, but with changes: load tantalum disulfide catalyst (100 mg) into tubular reactor rather than palladium sulfide catalyst.

Exs 22-23

Repeat Ex 21, but with changes: heat the tubular reactor to 900° C.; and 1000° C., respectively.

Comparative Example (Com Ex) A

Repeat Ex 1, but with changes: leave the tubular reactor empty rather than load palladium sulfide catalyst.

Com Exs B-E

Repeat Com Ex A, but with changes: heat the tubular reactor to 850° C.; 900° C.; 950° C.; and 1000° C., respectively.

Ethylene selectivity is calculated by the following formula:

$$\text{Ethylene selectivity} = \frac{2 \times \text{moles } C_2H_{4(output)}}{\text{moles } CH_{4(input)} - \text{moles } CH_{4(output)}} \times 100\%$$

Methane conversion is calculated by the following formula:

$$\text{Methane conversion} = \frac{\text{moles } CH_{4(input)} - \text{moles } CH_{4(output)}}{\text{moles } CH_{4(input)}} \times 100\%$$

TABLE 1

| Example number | Ethylene Selectivity (%) | Methane Conversion (%) |
|---|---|---|
| Ex 1 | 3.3 | 5.5 |
| Ex 2 | 4.9 | 5.8 |
| Ex 3 | 8.4 | 6.3 |
| Ex 4 | 9.5 | 8.2 |
| Ex 5 | 13.1 | 10.3 |
| Ex 6 | 0.6 | 7.9 |
| Ex 7 | 0.7 | 8.7 |
| Ex 8 | 1.1 | 9.1 |
| Ex 9 | 1.7 | 10.0 |
| Ex 10 | 1.9 | 12.6 |
| Ex 11 | 0.8 | 5.6 |
| Ex 12 | 1.5 | 6.6 |
| Ex 13 | 1.9 | 7.0 |
| Ex 14 | 2.4 | 7.9 |
| Ex 15 | 2.5 | 8.9 |
| Ex 16 | 2.1 | 2.8 |
| Ex 17 | 4.1 | 4.3 |
| Ex 18 | 4.6 | 7.1 |
| Ex 19 | 5.7 | 8.9 |
| Ex 20 | 6.9 | 13.2 |
| Ex 21 | 3.1 | 4.5 |
| Ex 22 | 5.3 | 7.5 |
| Ex 23 | 11.2 | 8.9 |

TABLE 2

| Comparative Example number | Ethylene Selectivity (%) | Methane Conversion (%) |
|---|---|---|
| Com Ex A | 2.4 | 2.6 |
| Com Ex B | 2.7 | 5.3 |
| Com Ex C | 3.2 | 5.7 |
| Com Ex D | 5.4 | 6.9 |
| Com Ex E | 5.8 | 7.9 |

The data in Table 1 show that the method disclosed herein forms ethylene. The data in Table 1 show that both methane conversion and ethylene selectivity increase with increased temperature.

Exs 24-25

Repeat Ex 1, but with changes: load 200 mg and 500 mg of palladium sulfide catalyst into tubular reactor, respectively, rather than 100 mg. The WHSV is 15000 mL·g$^{-1}$·h$^{-1}$ and 6000 mL·g$^{-1}$·h$^{-1}$, respectively.

Exs 26-27

Repeat Ex 6, but with changes: load 200 mg and 500 mg of molybdenum disulfide catalyst into tubular reactor, respectively, rather than 100 mg. The WHSV is 15000 mL·g$^{-1}$·h$^{-1}$ and 6000 mL·g$^{-1}$·h$^{-1}$, respectively.

Exs 28-29

Repeat Ex 11, but with changes: load 200 mg and 500 mg of ruthenium disulfide catalyst into tubular reactor, respectively, rather than 100 mg. The WHSV is 15000 mL·g$^{-1}$·h$^{-1}$ and 6000 mL·g$^{-1}$·h$^{-1}$, respectively.

Exs 30-31

Repeat Ex 16, but with changes: load 200 mg and 500 mg of titanium disulfide catalyst into tubular reactor, respectively, rather than 100 mg. The WHSV is 15000 mL·g$^{-1}$·h$^{-1}$ and 6000 mL·g$^{-1}$·h$^{-1}$, respectively.

TABLE 3

| Example number | Ethylene Selectivity (%) | Methane Conversion (%) |
|---|---|---|
| Ex 1 | 3.3 | 5.5 |
| Ex 6 | 0.6 | 7.9 |
| Ex 11 | 0.8 | 5.6 |
| Ex 16 | 2.1 | 2.8 |
| Ex 24 | 2.8 | 5.7 |
| Ex 25 | 2.1 | 6.2 |
| Ex 26 | 0.5 | 11.6 |
| Ex 27 | 0.4 | 13.6 |
| Ex 28 | 0.8 | 5.5 |
| Ex 29 | 1.1 | 7.0 |
| Ex 30 | 1.3 | 5.8 |
| Ex 31 | 0.5 | 9.3 |

The data in Table 3 show that methane conversion decreases with increased WHSV and that ethylene selectivity generally increases with increased WHSV. While not wishing to be bound to a particular theory, it is believed that the increase in ethylene selectivity can be attributed to a suppression of the over-oxidation product $CS_2$ via the presence of vaporized elemental sulfur, e.g., $S_2$.

Exs 32-34

Repeat Ex 1, but with changes: reduce the methane flow to 20 mL/min; 15 mL/min; 10 mL/min; and 5.0 mL/min, respectively, from the 25.0 mL/min methane flow of Example 1 to provide respective methane to sulfur ratios of 4.6:1.0; 3.5:1.0; and 2.3:1.0. A total methane/argon flow rate of 25 mL/min is maintained with argon balance gas.

Exs 35-37

Repeat Ex 6, but with changes: reduce the methane flow to 20 mL/min; 15 mL/min; 10 mL/min; and 5.0 mL/min, respectively, from the 25.0 mL/min methane flow of Example 6 to provide respective methane to sulfur ratios of 4.6:1.0; 3.5:1.0; and 2.3:1.0. A total methane/argon flow rate of 25 mL/min is maintained with argon balance gas.

Exs 38-40

Repeat Ex 11, but with changes: reduce the methane flow to 20 mL/min; 15 mL/min; 10 mL/min; and 5.0 mL/min, respectively, from the 25.0 mL/min methane flow of Example 11 to provide respective methane to sulfur ratios of 4.6:1.0; 3.5:1.0; and 2.3:1.0. A total methane/argon flow rate of 25 mL/min is maintained with argon balance gas.

Exs 41-43

Repeat Ex 16, but with changes: reduce the methane flow to 20 mL/min; 15 mL/min; 10 mL/min; and 5.0 mL/min, respectively, from the 25.0 mL/min methane flow of Example 16 to provide respective methane to sulfur ratios of 4.6:1.0; 3.5:1.0; and 2.3:1.0. A total methane/argon flow rate of 25 mL/min is maintained with argon balance gas.

Com Exs F-I

Repeat Com Ex A, but with changes: reduce the methane flow to 20 mL/min; 15 mL/min; 10 mL/min; and 5.0 mL/min, respectively, from the 25.0 mL/min methane flow of Com Ex A to provide respective methane to sulfur ratios of 4.6:1.0; 3.5:1.0; 2.3:1.0; and 1.2:1.0. A total methane/argon flow rate of 25 mL/min is maintained with argon balance gas.

Com Ex J

Repeat Ex 1, but with change: reduce the methane flow to 5.0 mL/min, from the 25.0 mL/min methane flow of Example 1 to provide a methane to sulfur ratio of 1.2:1.0. A total methane/argon flow rate of 25 mL/min is maintained with argon balance gas.

Com Ex K

Repeat Ex 6, but with change: reduce the methane flow to 5.0 mL/min, from the 25.0 mL/min methane flow of Example 1 to provide a methane to sulfur ratio of 1.2:1.0. A total methane/argon flow rate of 25 mL/min is maintained with argon balance gas.

Com Ex L

Repeat Ex 11, but with change: reduce the methane flow to 5.0 mL/min, from the 25.0 mL/min methane flow of Example 1 to provide a methane to sulfur ratio of 1.2:1.0. A total methane/argon flow rate of 25 mL/min is maintained with argon balance gas.

Com Ex M

Repeat Ex 16, but with change: reduce the methane flow to 5.0 mL/min, from the 25.0 mL/min methane flow of Example 1 to provide a methane to sulfur ratio of 1.2:1.0. A total methane/argon flow rate of 25 mL/min is maintained with argon balance gas.

TABLE 4

| Example number | Ethylene Selectivity (%) | Methane Conversion (%) |
|---|---|---|
| Ex 1 | 3.3 | 5.5 |
| Ex 6 | 0.6 | 7.9 |
| Ex 11 | 0.8 | 5.6 |
| Ex 16 | 2.1 | 2.8 |
| Ex 32 | 2.5 | 5.0 |
| Ex 33 | 1.3 | 4.6 |
| Ex 34 | 0.8 | 5.9 |
| Ex 35 | 0.6 | 7.0 |
| Ex 36 | 0.5 | 6.3 |
| Ex 37 | 0.3 | 5.3 |
| Ex 38 | 0.8 | 4.9 |
| Ex 39 | 0.7 | 4.8 |
| Ex 40 | 0.3 | 5.3 |
| Ex 41 | 1.6 | 4.1 |
| Ex 42 | 1.3 | 5.9 |
| Ex 43 | 0.4 | 6.2 |

TABLE 5

| Comparative Example number | Ethylene Selectivity (%) | Methane Conversion (%) |
|---|---|---|
| Com Ex A | 2.4 | 2.6 |
| Com Ex F | 2.1 | 4.1 |
| Com Ex G | 2.0 | 4.6 |
| Com Ex H | 1.3 | 4.8 |
| Com Ex I | 0.0 | 5.5 |

TABLE 5-continued

| Comparative Example number | Ethylene Selectivity (%) | Methane Conversion (%) |
|---|---|---|
| Com Ex J | 0.0 | 5.8 |
| Com Ex K | 0.0 | 4.8 |
| Com Ex L | 0.0 | 5.1 |
| Com Ex M | 0.0 | 6.8 |

The data in Table 4 show that over-oxidation to undesirable products is suppressed as the methane to sulfur ratio is increased, as seen by an increase in ethylene selectivity. The data in Table 5, corresponding to Com Exs A, and F-I show that the absence of the metal sulfide catalyst results in a process having a relatively lower methane conversion as the methane to sulfur ratio is increased. Additionally, the data in Table 5, corresponding to Corn Exs J-M show that ethylene selectivity at a methane to sulfur ratio of 1.2:1.0 is 0.0 percent.

What is claimed:

1. A method of forming ethylene comprising:
vaporizing elemental sulfur;
providing a metal sulfide catalyst;
supplying an inert gas to transport a mixture of methane and the vaporized elemental sulfur to the metal sulfide catalyst; and
contacting the metal sulfide catalyst with the mixture of methane and the vaporized elemental sulfur to form ethylene, wherein the mixture has a methane to sulfur molar ratio greater than 1.2:1.0 and a mass of the methane in grams per hour divided by a mass of the metal sulfide catalyst in grams has a value in a range of from 6000 mL·g$^{-1}$·h$^{-1}$ to 30000 mL·g$^{-1}$·h$^{-1}$.

2. The method of claim 1, wherein the metal sulfide catalyst is selected from the group consisting of palladium sulfide, palladium subsulfides, molybdenum sulfide, titanium sulfide, ruthenium sulfide, tantalum sulfide, or a combination thereof.

3. The method of claim 1, wherein the mixture of methane and the vaporized elemental sulfur has a methane to sulfur molar ratio in a range of from greater than 1.2:1.0 up to 8.5:1.0.

4. The method of claim 1, wherein the mixture of methane and the vaporized elemental sulfur has a methane to sulfur molar ratio in a range of from greater than 1.2:1.0 up to 5.8:1.0.

5. The method of claim 1, wherein contacting the metal sulfide catalyst with the mixture of methane and the vaporized elemental sulfur occurs at a temperature in range of from 200 degrees Celsius to 2000 degrees Celsius.

6. The method of claim 5, wherein contacting the metal sulfide catalyst with the mixture of methane and the vaporized elemental sulfur occurs at a temperature in range of from 825 degrees Celsius to 1325 degrees Celsius.

* * * * *